(12) United States Patent
Sahoo et al.

(10) Patent No.: US 11,471,821 B2
(45) Date of Patent: Oct. 18, 2022

(54) PROCESS FOR BIOGAS UPGRADATION

(71) Applicant: Indian Oil Corporation Limited, Maharashtra (IN)

(72) Inventors: Prakash Chandra Sahoo, Haryana (IN); Manoj Kumar, Haryana (IN); Suresh Kumar Puri, Haryana (IN); Sankara Sri Venkata Ramakumar, Haryana (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 17/232,853

(22) Filed: Apr. 16, 2021

(65) Prior Publication Data
US 2021/0322920 A1    Oct. 21, 2021

(30) Foreign Application Priority Data
Apr. 18, 2020  (IN) .............................. 202021016755

(51) Int. Cl.
| | | |
|---|---|---|
| *B01D 53/14* | (2006.01) | |
| *C01B 32/50* | (2017.01) | |
| *B01D 53/18* | (2006.01) | |
| *B01D 53/84* | (2006.01) | |
| *C12M 1/107* | (2006.01) | |
| *C12M 1/00* | (2006.01) | |
| *B82Y 30/00* | (2011.01) | |
| *B82Y 40/00* | (2011.01) | |

(52) U.S. Cl.
CPC ..... *B01D 53/1462* (2013.01); *B01D 53/1493* (2013.01); *B01D 53/18* (2013.01); *B01D 53/84* (2013.01); *C01B 32/50* (2017.08); *C12M 21/04* (2013.01); *C12M 47/18* (2013.01); *B01D 2252/20431* (2013.01); *B01D 2257/104* (2013.01); *B01D 2257/302* (2013.01); *B01D 2257/304* (2013.01); *B01D 2257/504* (2013.01); *B82Y 30/00* (2013.01); *B82Y 40/00* (2013.01)

(58) Field of Classification Search
CPC  B01D 53/1462; B01D 53/1493; B01D 53/18; B01D 53/84; B01D 2252/20431; B01D 3357/304; B01D 3357/504; C01B 32/50; C12M 24/04; C12M 47/18; B82Y 30/00; B82Y 40/00
USPC ....................................................... 423/228
See application file for complete search history.

(56) References Cited

U.S. PATENT DOCUMENTS

| | | | |
|---|---|---|---|
| 3,563,696 A | 2/1971 | Benson | |
| 4,405,577 A | 9/1983 | Sartori et al. | |
| 8,435,325 B2 | 5/2013 | Akiyama | |
| 2005/0003515 A1 | 1/2005 | Daly | |
| 2014/0056792 A1 | 2/2014 | Inoue et al. | |
| 2017/0232380 A1* | 8/2017 | Widger .............. | B01D 53/8671 |
| | | | 423/228 |
| 2018/0311611 A1 | 11/2018 | Vorberg et al. | |

FOREIGN PATENT DOCUMENTS

| | | |
|---|---|---|
| CN | 108568189 A | 9/2018 |
| DE | 102009009753 A1 | 9/2010 |
| EP | 2769759 | 8/2014 |
| WO | 2007141884 | 12/2007 |
| WO | 2015173234 A1 | 11/2015 |

OTHER PUBLICATIONS

Tippawong "Biogas quality upgrade by simultaneous removal of $CO_2$ and $H_2S$ in a packed column reactor" Science Direct, vol. 35, Issue 12, Dec. 2010 pp. 4531-4535.
Rongwong "Simultaneous absorption of $CO_2$ and $H_2S$ from biogas by capillary membrane contractor" Journal of Membrane Science, 2021 pp. 38-47.
Mandal "Simultaneous absorption of $CO_2$ and $H_2S$ into Aqueous Blends of N-Methyldiethanolamine and Diethanolamine".
Awe, Olumide Wesley et al., "A Review of Biogas Utilisation, Purification and Upgrading Technologies", Waste Biomass Valor, 2017, vol. 8, pp. 267-283.
Sreedhar et al., "Carbon Capture by Absorption—Path Covered and Ahead", Renewable and Sustainable Energy Reviews, 2017, vol. 76, pp. 1080-1107.
Kapoor, Rimika et al., "Evaluation of Biogas Upgrading Technologies and Future Perspectives: a Review", Environmental Science and Pollution Research, 2019, vol. 26, pp. 11631-11661.

* cited by examiner

*Primary Examiner* — Anita Nassiri-Motlagh
(74) *Attorney, Agent, or Firm* — Workman Nydegger

(57) ABSTRACT

The present invention relates to a biomimetic-hybrid solvent system for simultaneous capture of $H_2S$ and $CO_2$ from any gaseous composition. The present invention also relates to a process for upgradation of biogas to bio CNG by removing gaseous contaminants, including microbial removal of $H_2S$, to obtained purified $CO_2$. The biomimetic-hybrid solvent system contains three components selected from tertiary amine compounds, a functional colloidal fluid, and an enzyme mimic.

20 Claims, No Drawings

PROCESS FOR BIOGAS UPGRADATION

FIELD OF THE INVENTION

The present invention relates to a biomimetic-hybrid solvent system for simultaneous capture of $H_2S$ and $CO_2$ from any gaseous composition. The present invention also relates to a process for upgradation of biogas to bio-CNG by removing gaseous contaminants, including microbial removal of $H_2S$, to obtained purified $CO_2$. The biomimetic-hybrid solvent system contains three components selected from tertiary amine compounds, a functional colloidal fluid, and an enzyme mimic.

BACKGROUND OF THE INVENTION

Biogas results from anaerobic fermentation of organic waste. Raw biogas is a mixture of methane (70-80%) and carbon dioxide (20-30%) with hydrogen sulfide (0.005-3%), oxygen (0-1%), ammonia (<1%), trace amounts of siloxanes (0-0.02%), and moisture. It is a non-toxic, colorless, and flammable gas with an ignition temperature of 650-750° C. Its density is approximately 1.214 kg/m$^3$. Its calorific value is 20 MJ/m$^3$ (or 4700 kcal). To comply with the specifications of IS 16087:2016 bio-CNG, the concentration of major gaseous impurities such as $CO_2$ and $H_2S$ needs to be reduced to increase the heating value.

In the upgrading process, chemical absorption with amines has been identified as one of the most attractive processes for removal of $CO_2$ and $H_2S$. However, one of the major limitations of implementing amine-based $CO_2/H_2S$ removal from biogas is the high energy loss in the process. Nowadays, better process design and new solvents are developed to minimize the energy loss. The development of new solvents with enhanced characteristics has been an area of focus in recent times.

Further, to obtain highly pure $CO_2$ and to comply with the environmental norms, $H_2S$ must be removed from the desorbed solvent. Chemical methods have been used for $H_2S$ scrubbing from biogas.

In the scrubber using chemical process, the $H_2S$ containing gas is contacted in counter current mode with a scrubbing liquid, mostly NaOH solution or ferric chloride, and absorption of $H_2S$ occurs under alkaline conditions due to a chemical reaction of hydroxide ions with $H_2S$. The post scrubbing liquid containing the sulfide is directed to a bioreactor where the sulfide is oxidized into elemental sulfur and some amount of the caustic is regenerated. The drawback of this system is that it consumes a high amount of electricity and there is continuous usage of chemicals, thus leading to high O&M costs.

Few studies are available in literature which attempt to address one or more of these issues. However, they do not completely address all the above-mentioned pertinent issues. Herein, a process for the separation of $CO_2$ and $H_2S$ from any gaseous streams followed by purification of $CO_2$ has been described.

US20140056792A1 by Kansai Electric Power Co. Inc. and Mitsubishi Heavy Industries Engineering Ltd discloses an absorbent to absorb $CO_2$ or $H_2S$ contained in the flue gas emitted from a power generating plant such as a thermal plant and contains three or more amine compounds selected from linear or cyclic amine compounds having a primary amino group, and linear or cyclic amine compounds having a secondary amino group. A small amount of $CO_2$ contained in a large amount of boiler flue gas can be absorbed efficiently.

US 2005/0003515A1 by Individual discloses a system for removing $H_2S$ from methane ($CH_4$), which includes providing at least one biofilter cartridge that functions to sustain microbial activity which will function to consume $H_2S$ contained in a stream of methane gas.

EP2769759A1 by Kansai Electric Power Co. Inc. and Mitsubishi Heavy Industries Engineering Ltd discloses a process which consist of 1) a first amine, which is a straight chain secondary monoamine, 2) a second amine, which is a cyclic secondary polyamine as a reaction accelerator, and 3) a third amine, which is an amine consisting of one selected from a cyclic amine group constituted from a secondary or tertiary amino group or a straight chain amine group with high steric hindrance and are mixed to obtain an absorbent. By the synergistic effect thereof, absorption properties to $CO_2$ and/or $H_2S$ are excellent and the absorbed $CO_2$ or $H_2S$ emission properties during the regeneration of the absorbent become excellent. Therefore, the water vapor amount used during the regeneration of the absorbent in $CO_2$ recovery equipment can be reduced.

U.S. Pat. No. 4,405,577A by ExxonMobil Research and Engineering Co., describes an invention that relates to an alkaline promoter system comprising specific mixtures of non-sterically hindered amino compounds and sterically hindered amino acids and their use in acid gas scrubbing processes.

U.S. Pat. No. 3,563,696A by Union Carbide Corporation discloses a process of improved thermal efficiency and lower capital cost for separating $CO_2$ and/or $H_2S$ from gaseous mixtures using a regenerable aqueous alkaline scrubbing solution which is circulated in a cyclic process between absorption and regeneration stages.

WO2007141884A1 by Mitsubishi Heavy Industries Engineering Ltd and Kansai Electric Power Co. Inc. describes an absorbent liquid capable of absorbing $CO_2$ or $H_2S$ or both from a gas, comprising an alkanolamine as a first compound component and a second component of a nitrogenous compound having two or more primary, secondary, or tertiary nitrogen or having all thereof in each molecule. This absorbent liquid exhibits excellent absorptive capacity, performance/absorption reaction, and heat performance as compared with those of aqueous solutions wherein equal wt. % concentrations of alkanolamine and nitrogenous compound are contained alone, and can recover $CO_2$ or $H_2S$ or both, from a gas with reduced energy.

U.S. Pat. No. 8,435,325B2 by Mitsubishi Hitachi Power Systems Ltd discloses a method and a device for removing acidic materials, such as $CO_2$ and $H_2S$, in a gas purifying process by contacting gas including $CO_2$ and $H_2S$, such as natural gas, coal seam gas, and gas gasified from heavy oil, with rich solution. The method and the device can reduce the regeneration energy for the rich solution and obtain a treated gas having substantially no $H_2S$ concentration.

In the paper "Simultaneous Absorption of $CO_2$ and $H_2S$ Into Aqueous Blends of N-Methyl diethanolamine and Diethanolamine" Environ. Sci. Technol., 2006, 40 (19), pp 6076-6084, Mandal et al., studied a broad spectrum of alkanolamines and, their mixtures for the removal of acid gases such as $CO_2$, $H_2S$, and COS from natural and industrial gas streams.

In the paper titled "Simultaneous absorption of $CO_2$ and $H_2S$ from biogas by capillary membrane contactor" Rongwong et al. studied the simultaneous absorption of $H_2S$ and $CO_2$ from biogas using a capillary membrane contactor. The synthetic biogas contained 250-1000 ppm $H_2S$, 20-40% $CO_2$ and $CH_4$. The absorbents used were water and monoethanolamine (MEA) solution.

In another paper titled "Biogas quality upgrade by simultaneous removal of $CO_2$ and $H_2S$ in a packed column reactor" Energy, 35, 2010, 4531-4535, N. Tippayawong et al. studied a biogas purification process. Typical biogas contains 50-65% methane ($CH_4$), 30-45% carbon dioxide ($CO_2$), moisture and traces of hydrogen sulfide ($H_2S$). The aqueous solutions employed were sodium hydroxide (NaOH), calcium hydroxide ($Ca(OH)_2$) and mono ethanolamine (MEA). Liquid solvents were circulated through the column, contacting the biogas in countercurrent flow. Test results revealed that the aqueous solutions used were effective in reacting with $CO_2$ in biogas (over 90% removal efficiency), creating $CH_4$ enriched fuel. $H_2S$ was removed to below the detection limit.

The drawbacks of the above-mentioned processes are:
There is only a provision for removal of either $CO_2$ or $H_2S$
A high temperature is required for solvent regeneration
High concentration amine solution required
Higher amine degradation
High operating cost
High pure $CO_2$ regeneration is not possible
High water requirement for $H_2S$ scrubbing The present invention overcomes the above-mentioned drawbacks and discloses an efficient solvent system for simultaneous capture of $H_2S$ and $CO_2$ from any gaseous composition, followed by sustainable microbial removal of $H_2S$ to obtained purified $CO_2$.

SUMMARY OF THE INVENTION

There are several processes known in the art for the separation of $CO_2$ and $H_2S$ from any gaseous streams followed by purification of $CO_2$. However, there are certain drawbacks attached to these processes. Therefore, a solvent system for simultaneous capture of $H_2S$ and $CO_2$ from any gaseous composition, followed by sustainable microbial removal of $H_2S$ to obtained purified $CO_2$ seems to overcome the drawbacks mentioned in the art. Hence, a biomimetic-hybrid solvent system for simultaneous capture of $H_2S$ and $CO_2$ from any gaseous composition is highly desirable.

OBJECTIVES OF THE INVENTION

It is the main objective of the present invention to provide a process for upgradation of biogas to bio-CNG by simultaneous separation of H2S and CO2 from a gaseous composition. The process comprises synthesis of a biomimetic-hybrid solvent system; evaluation of the biomimetic hybrid solvent system; and biological removal of H2S to generate purified CO2.

Further, the object of this invention is providing biomimetic-hybrid solvent system comprising synthesis of a liquid colloidal nanoparticle; development of a selective biomimetic complex; and addition of at least one tertiary amine solvent.

Further, the object of the invention is to provide biological removal of H2S to generate purified CO2 comprising the steps of:
a) desorbed H2S and CO2 from the gaseous composition is fed to bottom of a biological scrubber;
b) water is sprayed from top of the biological scrubber and re-circulated to keep the media moist;
c) CO2 and traces of O2 is collected from top of the biological scrubber and passed through an electrochemical cell;
d) H2S is removed from the scrubber; and
e) O2 is removed electrochemically to obtain high pure CO2.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps of the process, features of the system, referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have their meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally equivalent products and methods are clearly within the scope of the disclosure, as described herein.

The present invention provides a process for the simultaneous separation of CO2 and H2S from gaseous streams, in particularly from raw biogas. The present invention also provides a biomimetic-hybrid solvent system for simultaneous capture of CO2 and H2S from a gaseous composition.

In an embodiment of the invention, a process for upgradation of biogas to bio-CNG by simultaneous separation of H2S and CO2 from a gaseous composition is disclosed. The process comprises synthesis of a biomimetic-hybrid solvent system; evaluation of the biomimetic hybrid solvent system; and biological removal of H2S to generate purified CO2.

In an embodiment of the invention, the biomimetic-hybrid solvent system comprises a tertiary amine solvent, a functional colloidal fluid, and an enzyme mimic.

In another embodiment of the invention, the biomimetic-hybrid solvent system comprises synthesis of a liquid colloidal nanoparticle; development of a selective biomimetic complex; and addition of at least one tertiary amine solvent.

In another embodiment of the invention, an efficient biomimetic-hybrid solvent system was synthesized for higher $CO_2$ and $H_2S$ loading capacity as compared to amines and other physical solvents, and desorption was carried out at low temperature. The desorbed gas was then entered into a biological scrubber to remove $H_2S$ and to obtain purified $CO_2$. The biomimetic-hybrid solvent system described in the present invention was used for $CO_2$ and $H_2S$ capture and their regeneration followed by $H_2S$ removal to obtain purified $CO_2$ involves the following steps:

A. Synthesis of biomimetic-hybrid solvent system:
1. Synthesis of liquid like colloidal nanoparticle
2. Functionalization of colloidal nanoparticle described in step-1 with at least one aromatic amine group and at least one hydrophobic alcohol group having chain length from C5-C14
3. Development of selective biomimetic complexes
4. Syntheses of enzyme mimic nano-colloid with at least one biomimetic complex
5. Addition of at least one tertiary amine solvent
6. Biomimetic-hybrid solvent system was formulated by suitable combination of solvent system described in step-2, step-4, and step-5

B. Evaluation of biomimetic-hybrid solvent system-biomimetic-hybrid solvent system prepared in step-6 was evaluated by the following steps:
7. $CO_2$ and $H_2S$ absorption from gaseous mixture or raw biogas using hybrid solvent at different conditions were monitored by two methods: gravimetric and pressure drop method
8. Viscosity monitoring after $CO_2$ and $H_2S$ loading
9. Corrosion monitoring
10. Desorption of $CO_2/H_2S$ and regeneration of amine has been monitored by gravimetric method
11. Recycling of $CO_2$ lean solvent C. Biological removal of $H_2S$ and generate purified $CO_2$:
12. The desorbed $CO_2$ and $H_2S$ mixture were fed to the bottom of a biological scrubber operating at room temperature and at a pressure normally ranging from 1 to 1.2 atm
13. The biological scrubber described in step-12 contains biofilm of microbes immobilized on support material
14. The microbes described in step-13 have the capability to oxidize $H_2S$, $HS^-$, $S$ and $S_2O_3$
15. Water is sprayed from the top of the biological scrubber and re-circulated to keep the media moist
16. $CO_2$ and traces of $O_2$ was collected from the top and passed through the electrochemical cell
17. The electrochemical $O_2$ removal to obtain high pure $CO_2$.

In an embodiment of the present invention, the liquid like colloidal nanoparticle used in step-1 and 4 may include any colloidal nano particles that contain one or more Lewis acid colloid. Examples of colloidal nano particles may include but are not limited to $Al_2O_3$, $TiCl_2$/Nano-γ-$Al_2O_3$, $CoFe_2O_4$, $SO_3H-$ functionalized magnetic $Fe_3O_4$, $Ga_2O_3$, functional silica, colloidal $In_2O_3$, $ZnO$, $CoO$, $MnO_2$, $Fe_3O_4$, $PbS$, $MFe_2O_4$ (M=Fe, Co, Mn, Zn), Lewis acid $ZrO_2$, silica boron sulfuric acid nanoparticles, Ni metal nanoparticles loaded on the acid-base bifunctional support ($Al_2O_3$), $Co_3O_4$ Nanoparticle. The amount of colloidal nanoparticle may be varied between 500-1000 ppm for step-1, and 50-100 ppm for step-4.

In another embodiment of the present invention, the functional aromatic amines may include 2,4-Diaminotoluene, 2,4-diaminoethylbenzene, 2-Naphthylamine, 1-Naphthylamine, N-Phenyl•2•naphthylamine, N-hydroxy-1-naphthylamine, N-hydroxy-2-naphthylamine, 1-Amino-2-naphthyl sulfate, 1-Amino-4-naphthyl sulfate, 1-Amino-2-naphthyl glucuronide, 1-Amino-4-naphthyl glucuronide, 4-Aminobiphenyl, N-hydroxy-4-aminobiphenyl, methyl (tri-o-acetyl-d-D-glucopyranosyl bromide), N,4-biphenyl-N-hydroxy-, B-glucuroniosylamine, Benzidine, 3,3'-Dichlorobenzidine, 4-Amino-2-nitrophenol, 1,2-diamino-4-nitrobenzene, and 1,4-diamino-2-nitrobenzene, 4,4'-Methylenedianiline (MDA), 4,4'-Methylene-bis-(2-chloroaniline), 2,2'-bis (4-Aminophenyl) propane, 4,4'-Imidocarbonyl-bis (N,N'-Dimethyl) Aniline.

In yet another embodiment, members of hydrophobic alcohol group include hexan-1-ol, octan-1-ol and decan-1-ol and a combination thereof.

In another embodiment, the bio mimic catalysts comprising of tripodal ligand system and macro-cyclic ligand systems can be used. The ligands mainly consists of 1-(3-Aminopropyl)-2-methyl-1H-imidazole and glutaraldehyde, 3-(2-Ethyl-1H-imidazol-1-yl)propan-1-amine and glutaraldehyde, 2-(4,5-Dimethyl-1H-imidazol-1-yl)ethanamine dihydrochloride and glutaraldehyde, 3-(2-isopropyl-imidazol-1-yl)-propylamine and glutaraldehyde.

The metal can be varied as Zn, Cu, Ni, Cd or Ln. The immobilized biomimetic complex can be altered from 0 to 300 mg/g of the immobilization matrix.

The tertiary amine solvents used in one or more process steps of the present invention include but are not limited to one or more of the following: the hydrochloride, sulfate, nitrate salt of Isobutyl amine, 2-amino-2-methyl-ipropanol (AMP), 2-(2-aminoethylamino)ethanol (AEE), 2-amino-2-hydroxymethyl-i,3-propanediol (Tris), N-methyldiethanolamine (MDEA), dimethyl monoethanolamine (DMMEA), diethyl monoethanolamine (DEMEA), triisopropanolamine (TIPA) and triethanolamine), trimethylamine, triethylamine, tripropylamine, tributylamine, dimethyl ethylamine, dimethyl propylamine, dimethyl butylamine, diethyl methylamine, diethyl propylamine, diethyl butylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3,3-dimethylbutylamine, N,N-dimethylbutylamine.

In an embodiment the total concentration of tertiary amine will be at 5-10 wt %. In another embodiment the enzyme mimic nano-colloid amount may be varied between 100-500 ppm.

In another embodiment it was found that the biomimetic-hybrid solvent shows higher $CO_2$ and $H_2S$ loading activity with intermittent dosing of enzyme mimic nano-colloid with at least one biomimetic complex. With dosing rate of 0.6 ml-0.8 ml/2 days there is an enhancement of 7-8% loading of $CO_2$ and $H_2S$.

Yet in another embodiment, the biomimetic-hybrid solvent described herein is their resistance to an increase in viscosity during absorption of the gaseous species.

The enzyme mimic nano-colloid concentration can be varied depending on the % of $H_2S$ in the feed gas. For example, for every increase in 5 ppm of $H_2S$, 100 ppm enzyme mimic nano-colloid needs to be added to maintain the viscosity between 1.33 and 1.75 η/mPa·s. In some embodiments, the viscosity is substantially maintained or may even decrease.

In yet another embodiment, different H2S/CO2 sources have been used for the capture. In this process, carbon dioxide containing flue gas, or process gas or gas from biomethanation plants can be used. The CO2 concentration can be varied from 200 ppm to 30% in the source gas and H2S concentration can be varied between 50-3000 ppm.

In another embodiment, the resulting gas can be passed through the solvent medium through in any suitable device forming fine dispersion of gas result in an increase in contact area. The gas may be sparged in micro-bubble or nano-bubble size.

In another embodiment, the pressure of raw gas containing CO2 and H2S can vary from 0.1 bar to 0.3 bar and temperature can be varied between 20-55° C. In another embodiment, the corrosion activity was studied for 0-60 days in a stainless vessel by analysis the leaching metal ion in the solvent. In yet another embodiment, the H2S/CO2 desorption was carried out by gravimetric method.

In accordance with the invention, the viscosity of the hybrid solvent system has been analyzed for a period of 100 cycles and no change in viscosity was observed.

In another embodiment the bio-scrubber support material may include but are not limited to peat, silica with size ranging from 2-10 mm, activated alumina with size from 10-20 mm, compost material, soil, activated carbon, synthetic polymers, synthetic hydrogels, and porous rocks. The biofilter support material may furthermore take a variety of forms such as cylindrical pellets, spheres, Raschig rings, irregular shapes, hollow tubes, or fibers.

The bio scrubber support material needs to be moist with an aqueous solution and the surfaces of the support material are preferably porous. The support material must be such that microorganisms immobilized on it. The moisture can be given in the form of water or mist.

In accordance with the invention, the microorganisms are critical to this invention. The microbes may include *Lysinibacillus* sp. (MTCC 5666) and its mutants.

Besides that, several other species from genera *Thiobacillus* can be used. These may include *Thiobacillus halophilus, Thiobacillus thioparus, Thiobacillus ferrooxidans, Thiobacillus thiooxidans, Thiobacillus denitrifican, Pseudomonas* sp, *Arthobacter* sp., *Bacillus* sp. and their combination. These microbes are available to the public. The microorganisms described in the current invention can work in a broad pH ranging from 3-12.

The media composition of the bio-scrubber includes (g L-1): NaHCO3 3.50, NH4Cl 1.00, K2HPO4 0.15, KH2PO4 0.12, MgCl2.7H2O, 0.2 and CaCl2 0.02, along with a trace element solution (g L-1: H3BO3 2.86, ZnCl.7H2O 0.22, MnCl2.4H2O 1.4, CoCl2.H2O 0.01, Na2MoO4.2H2O 0.39).

In another embodiment the gas retention time in the biogas should be kept between 5-9 seconds.

In another embodiment the 100-500 ppm O2 should be passed through the bio-scrubber for the microbial survival.

In another embodiment the outlet of the bio-scrubber containing CO2 and O2 is passed through an integrated electrochemical O2 removal system. The cathode of which consist of perforated graphite particles, and anode consist of stainless steel or titanium particles. The cathode and anode must be separated by H+ exchange membrane like Nafion.

EXAMPLES

Having described the basic aspects of the present invention, the following non-limiting examples illustrate specific embodiment thereof. Those skilled in the art will appreciate that many modifications may be made in the invention without changing the essence of invention.

Example 1—H2S and CO2 Removal from Biogas Followed by H2S Removal Using Bio-Scrubber to Obtain High Purified CO2

1. Synthesis of Biomimetic-Hybrid Solvent System
  a. 5 ml of 4, 4'-Imidocarbonyl-bis (N, N'-Dimethyl) Aniline was dissolved in a 20 ml volume of ethanol followed by the addition of NaN3 (200 mg/L). To the solution 2 mM hexan-1-ol was added followed by constant stirring.
  b. One gram of Al2O3 NPs having size less than 50 nm was prepared by a method described in the prior art and added to the above solution allowed to shake for 3 days.
  c. The mixture was then centrifuged to remove the supernatant. An additional 100 mL of the ethanol solution followed by 50 mM of 2-(4,5-Dimethyl-1H-imidazol-1-yl)ethanamine dihydrochloride and 50 mM Zinc acetate were added to the initially coated Al2O3 NPs and allowed to equilibrate for 3 more days.
  d. The mixture was then centrifuged at 12000 g followed by repeated washing with deionized water to remove the unabsorbed biomimetic complex.
  e. Then, the coated Al2O3 NPs were redispersed in 100 mL of deionized water to make the stock suspensions.
  f. The final biomimetic-hybrid solvent was prepared by adding 10 wt % 2-amino-2-methyl-ipropanol and 100 ppm of enzyme mimic Al2O3 NPs.

2. Evaluation of Biomimetic-Hybrid Solvent System for Biogas Purification
Synthetic biogas having 25 vol. % CO2, 75 vol. % CH4 and 1000 ppm H2S was prepared and used for experiment.
  a. For biogas purification experiment by the synthesized biomimetic-hybrid solvent system as described in step-1, Synthetic biogas was flown into a reactor (100 mL) containing 20 g of solvent at a flow rate of 20 mL min-1 at 30° C. and 1 atm. The weight percent of acid gas absorbed was determined by weighing the solvent at a regular interval using an electronic balance with an accuracy of ±0.1 mg.
  b. When the commercially used solvent like Methyl diethanolamine (N-methyl-diethanolamine) and piperazine (30% MDEA/PZ) was used, a CO2/H2S uptake of 2.9 mol/l was observed after 30 min. Further, when the biomimetic-hybrid solvent was used, a maximum acid gas uptake of 4.9 mol/l was observed.
  c. Desorption of acid gas (CO2/H2S) from biomimetic-hybrid solvent was carried out by heating the reactor column at 90° C. for 1 h. The results confirmed that ~95% desorption is possible with 100 times of recyclability of the solvent.
  d. The outlet gas in the disrober unit was analyzed by GC and found to contain 98% CO2 and 2% H2S.
  e. The methane content from the reactor was analyzed and found to be higher than 96%.

3. Biological Removal of H2S and Generate Purified CO2
  a. A bio-scrubber was prepared using an absorption column of 200 mL (5 cm inner diameter, 300 mm height).
  b. Plastic media separated by silica layers were placed in the column for microbial immobilization.
  c. Ultra fine mist was circulated by 3 openings to the column to keep the media moist.
  d. 100 ml of nutrient media composed of (g L-1): NaHCO3 3.50, NH4Cl 1.00, K2HPO4 0.15, KH2PO4 0.12, MgCl2.7H2O, 0.2 and CaCl2 0.02, along with a trace element solution (g L-1: H3BO3 2.86, ZnCl.7H2O 0.22, MnCl2.4H2O 1.4, CoCl2.H2O 0.01, Na2MoO4.2H2O 0.39) were added along with 10 ml of microbial culture (*Lysinibacillus* sp. (MTCC 5666)) having CFU=$5.8 \times 10^{11}$.

e. After 5 days of growth period the scrubber was used for gas purification.

f. Desorbed gas containing 98% CO2 and 2% H2S were fed at the bottom of the column at flow rates from 0.08 to 0.2 L min-1, along with 200 ppm O2, yielding gas residence times (GRT) in the absorption column from 5 to 7 second.

g. The concentrations of S—, SO42-, S2-, inorganic carbon, in the liquid phase were periodically measured as well as the dissolved oxygen.

h. The outlet of the bio-scrubber containing CO2 and trace of O2 was then passed through an integrated electrochemical O2 removal system with a flow rate of 5 ml/s. The cathode of which consist of 80 cm3 perforated graphite particles, and anode consist of 50 cm2 stainless steel rod. The cathode and anode must be separated by H+ exchange Nafion membrane. The voltage was fixed as 1.9V.

i. The outlet gas was collected and found to contain 99.5% CO2 by GC analysis.

Table 1 below discloses the input and output biogas composition.

TABLE 1

Input and output biogas composition

| Solvent system | Input Biogas composition | Output methane recovery |
|---|---|---|
| Biomimetic Hybrid solvent: | CH4 (50 V %) | CH4 (99.1 V %) |
| | CO2 (49.9 V %) | CO2 (0.9 V %) |
| | H2S (1000 ppm) | H2S (N.D) |
| | CH4 (60 V %) | CH4 (99.3 V %) |
| | CO2 (39.9 V %) | CO2 (0.7 V %) |
| | H2S (1000 ppm) | H2S (N.D) |
| | CH4 (70 V %) | CH4 (99.3 V %) |
| | CO2 (29.9 V %) | CO2 (0.7 V %) |
| | H2S (1000 ppm) | H2S (N.D) |
| | CH4 (80 V %) | CH4 (99.8 V %) |
| | CO2 (19.9 V %) | CO2 (0.2 V %) |
| | H2S (1000 ppm) | H2S (N.D) |

The invention claimed is:

1. A process for simultaneously separating $H_2S$ and $CO_2$ from a gaseous composition, the process comprising:
   synthesizing liquid colloidal nanoparticles;
   functionalizing liquid colloidal nanoparticles with at least one aromatic amine group and at least one hydrophobic alcohol group, wherein the at least one hydrophobic alcohol group has a chain length from $C_5$-$C_{14}$;
   adding a metal salt to a ligand to form a biomimetic complex, wherein the ligand comprises an imidazole group;
   adding the functionalized liquid colloidal nanoparticles to the biomimetic complex;
   adding at least one tertiary amine to form a biomimetic hybrid solvent; and
   passing the gaseous composition through a reactor comprising the biomimetic hybrid solvent, wherein the biomimetic hybrid solvent is characterized to absorb and simultaneously remove $H_2S$ and $CO_2$ from the gaseous composition.

2. The process as claimed in claim 1, wherein the gaseous composition comprises raw biogas, and wherein simultaneous separation of $H_2S$ and $CO_2$ from the raw biogas upgrades the raw biogas to bio CNG.

3. The process as claimed in claim 1, wherein synthesizing the liquid colloidal nanoparticles comprise synthesizing $Al_2O_3$, $TiCl_2$/Nano-$\gamma$-$Al_2O_3$, $CoFe_2O_4$, $SO_3H$-functionalized magnetic $Fe_3O_4$, $Ga_2O_3$, functional silica, colloidal $In_2O_3$, ZnO, CoO, $MnO_2$, $Fe_3O_4$, PbS, Lewis acid $ZrO_2$, silica boron sulfuric acid nanoparticles, Ni metal nanoparticles loaded on the acid-base bifunctional $Al_2O_3$ support, $Co_3O_4$ nanoparticles, or $M_2O_4$, wherein M is Fe, Co, Mn, or Zn in an amount of 500-1000 ppm.

4. The process as claimed in claim 1, wherein functionalizing the liquid colloidal nanoparticles with at least one aromatic amine group comprises functionalizing with 2,4-diaminotoluene, 2,4-diaminoethylbenzene, 2-naphthylamine, 1-naphthylamine, N-phenyl-2-naphthylamine, N-hydroxy-1-naphthylamine, N-hydroxy-2-naphthylamine, 1-Amino-2-naphthyl sulfate, 1-amino-4-naphthyl sulfate, 1-amino-2-naphthy 1 glucuronide, 1-amino-4-naphthyl glucuronide, 4-aminobiphenyl, N-hydroxy-4-aminobiphenyl, methyl (tri-o-acetyl-d-D-glucopyranosyl bromide), N,4-biphenyl-N-hydroxy-,B-glucuroniosylamine, benzidine, 3,3'-dichlorobenzidine, 4-amino-2-nitrophenol, 1,2-diamino-4-nitrobenzene, and 1,4-diamino-2- nitrobenzene, 4,4'-methylenedianiline (MDA), 4,4'-M ethylene-bis-(2-chloroaniline), 2,2'-bis (4-Aminophenyl) propane, or 4,4'-imidocarbonyl-bis (N,N'-dimethyl) aniline.

5. The process as claimed in claim 1, wherein functionalizing the liquid colloidal nanoparticles with at least one hydrophobic alcohol group having chain length from $C_5$-$C_{14}$ comprises functionalizing with hexan-1-ol, octan-1-ol and decan-1-ol or a combination thereof.

6. The process as claimed in claim 1, wherein adding a metal salt to a ligand having an imidazole group to form a biomimetic complex comprises adding Zn, Cu, Ni, Cd or Ln to 1-(3-Aminopropyl)-2-methyl-1H-imidazole and glutaraldehyde, 3-(2-Ethyl-1H-imidazol-1-yl)propan-1-amine and glutaraldehyde, 2-(4,5-Dimethyl-1H-imidazol-1-yl) ethanamine dihydrochloride and glutaraldehyde, or 3-(2-isopropyl-imidazol-1-yl)-propylamine and glutaraldehyde.

7. The process as claimed in claim 1, wherein adding at least one tertiary amine to form a biomimetic hybrid solvent comprises adding a salt of hydrochloride, a sulfate, a nitrate of isobutyl amine, 2-amino-2-methyl-ipropanol (AMP), 2-(2-aminoethylamino)ethanol (AEE), 2-amino-2-hydroxymethyl-i,3-propanediol (Tris), N-methyldiethanolamine (MDEA), dimethyl monoethanolamine (DMMEA), diethyl monoethanolamine (DEMEA), triisopropanolamine (TIPA) and triethanolamine), trimethylamine, triethylamine, tripropylamine, tributylamine, dimethyl ethylamine, dimethyl propylamine, dimethyl butylamine, diethyl methylamine, diethyl propylamine, diethyl butylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3,3-dimethylbutylamine, or N,N-dimethylbutylamine.

8. The process as claimed in claim 1, wherein adding at least one tertiary amine to form a biomimetic hybrid solvent comprises adding 5-10 wt % of the at least one tertiary amine of weight of the biomimetic hybrid solvent.

9. The process as claimed in claim 1, wherein adding the functionalized liquid colloidal nanoparticles to the biomimetic complex comprises adding about 100-500 ppm of the functionalized liquid colloidal nanoparticles.

10. The process as claimed in claim 1, wherein passing the gaseous composition through the reactor comprises sparging the gaseous composition as a fine dispersion having a size of a micro-bubble or a nano-bubble.

11. The process as claimed in claim 2, wherein the raw biogas comprises 75 vol. % $CH_4$ before passing through the reactor and exiting bio CNG comprises 96% $CH_4$ while leaving the reactor.

12. The process as claimed in claim 1, further comprises monitoring absorption of $H_2S$ and $CO_2$ by the biomimetic hybrid solvent using a gravimetric method or a pressure drop method.

13. The process as claimed in claim 1, further comprises heating the reactor to a temperature of 90° C. for an hour to desorb $H_2S$ and $CO_2$ from the biomimetic hybrid solvent.

14. The process as claimed in claim 13, wherein heating the reactor results in about 95% of desorption of $H_2S$ and $CO_2$ from the biomimetic hybrid solvent with about 100 times of recyclability of the biomimetic hybrid solvent, and wherein desorbed gas comprises 98% $CO_2$, and 2% $H_2S$.

15. The process as claimed in claim 14, further comprising feeding the desorbed $CO_2$ and $H_2S$ to a bottom of a biological scrubber operating at room temperature and at a pressure ranging from 1 to 1.2 atm.

16. The process as claimed in claim 15, wherein the biological scrubber comprises a biofilm, wherein the biofilm comprises microbes immobilized on a support material.

17. The process as claimed in claim 16, wherein the support material is peat, silica with size ranging from 2-10 mm, activated alumina with size from 10-20 mm, compost material, soil, activated carbon, synthetic polymers, synthetic hydrogels, or porous rocks, and wherein the support material is in a form of cylindrical pellets, spheres, Raschig rings, irregular shapes, hollow tubes, or fibers.

18. The process as claimed in claim 16, wherein the microbes comprise *Thiobacillus halophilus, Thiobacillus thioparus, Thiobacillus ferrooxidans, Thiobacillus thiooxidans, Thiobacillus denitrifican, Pseudomonas* sp, *Arthobacter* sp., *Bacillus* sp. and a combination thereof, wherein the microbes oxidize $H_2S$ to HS—, S and $S_2O_3$.

19. The process as claimed in claim 15, further comprising passing about 100-500 ppm $O_2$ through the biological scrubber for the microbes to survive.

20. The process as claimed in claim 19, further comprising passing $CO_2$ and $O_2$ through an electrochemical cell to remove $O_2$ and result in pure $CO_2$.

* * * * *